(12) United States Patent
Kojima

(10) Patent No.: US 6,997,038 B2
(45) Date of Patent: Feb. 14, 2006

(54) GAS SENSOR HAVING IMPROVED STRUCTURE FOR INSTALLATION OF PROTECTIVE COVER

(75) Inventor: Takashi Kojima, Kasugai (JP)

(73) Assignee: Denso Corporation, Aichi-Pref. (JP)

( * ) Notice: Subject to any disclaimer, the term of this patent is extended or adjusted under 35 U.S.C. 154(b) by 403 days.

(21) Appl. No.: 09/817,133

(22) Filed: Mar. 27, 2001

(65) Prior Publication Data

US 2001/0027679 A1    Oct. 11, 2001

(30) Foreign Application Priority Data

Mar. 27, 2000  (JP)  ............................. 2000-085613
Jan. 29, 2001  (JP)  ............................. 2001-020643

(51) Int. Cl.
*G01M 15/00* (2006.01)
(52) U.S. Cl. ..................................... 73/23.31; 73/23.31
(58) Field of Classification Search ........ 204/421–429; 73/23.31, 31.05, 1.06, 40.5 A, 31.06, 23.4, 73/23.32

See application file for complete search history.

(56) References Cited

U.S. PATENT DOCUMENTS 5,238,552 A    8/1993   Kato et al.
5,880,353 A    3/1999   Graser et al.
6,214,186 B1 * 4/2001   Wanatabe et al. ........... 204/428

FOREIGN PATENT DOCUMENTS

| EP | 0933630 | 8/1999 |
|----|---------|--------|
| EP | 0974836 | 1/2000 |
| EP | 0978721 | 2/2000 |
| EP | 0979996 | 2/2000 |
| JP | 09-304332 | 11/1997 |
| JP | 10170474 | 6/1998 |
| JP | 11-505029 | 5/1999 |
| JP | 2000-171429 | 6/2000 |

* cited by examiner

Primary Examiner—David A Zarneke
Assistant Examiner—Monica D. Harrison
(74) Attorney, Agent, or Firm—Nixon & Vanderhye PC

(57) ABSTRACT

An improved structure of a gas sensor is provided which is designed to provide for firm installation of the protective cover assembly on a cover mount of a housing. The cover assembly made up of an outer cylindrical cover and an inner cylindrical cover each of which includes an open end portion and a body portion. The body portion of the inner cylindrical cover is disposed within the body portion of the outer cylindrical cover in a non-contact fashion. The open end portion of at least one of the outer and inner cylindrical covers has a shoulder which is placed in line contact with the open end portion of the other cylindrical cover to secure portions of the outer and inner cylindrical covers installed on an end side wall of the housing.

8 Claims, 9 Drawing Sheets

GAS SENSOR HAVING IMPROVED STRUCTURE FOR INSTALLATION OF PROTECTIVE COVER

BACKGROUND OF THE INVENTION

1. Technical Field of the Invention

The present invention relates generally to a gas sensor which may be employed in an air-fuel ratio control system for automotive vehicles for measuring the concentration of gas such $O_2$, NOx, or CO, and more particularly to an improved structure of such a gas sensor which provides for ease of installation of a protective cover on a cover mount, firm engagement of the protective cover with the cover mount, and ease of machining of the cover mount.

2. Background Art

Typical air-fuel ratio feedback control systems for automotive internal combustion engines usually employ the concentration of oxygen contained in exhaust gasses measured by a gas sensor installed in an exhaust system. A gas sensor of such a type usually includes a hollow cylindrical housing, a sensor element disposed within the housing, and a protective head cover projecting from an end of the housing to cover a head of the sensing element. The protective head cover is made of a metallic member for protecting the fragile sensor element against undesirable impacts and usually has a double walled structure consisting of an outer and an inner cover wall.

The installation of the outer and inner cover walls on the housing is accomplished by placing ends of the outer and inner cover walls so as to overlap each other on a side surface of an end portion of the housing and laser-welding the periphery of the ends of the outer and inner cover walls to the housing.

For example, Japanese Patent First Publication No. 9-304332 teaches such installation which will be discussed below with reference to FIG. 11.

A gas sensor 9 includes a housing 10, a cup-shaped sensing element 29, an outer cover wall 91, and an inner cover wall 92 which have dimples 911 and 921 formed in bottoms 910 and 920 thereof. The inner cover wall 92 is fitted within the outer cover wall 91 in engagement of the dimple 921 with the dimple 911.

The housing 10 has a small-diameter portion 15 formed on an end portion 106 thereof. The outer and inner cover walls 91 and 92 have open end portions 915 and 925 which are so formed as to be lapped one over the other when the inner cover wall 92 is fitted within the outer cover wall 91 in engagement of the dimple 921 with the dimple 911. The open end portions 915 and 925 are welded as indicated at 14, to the periphery of a side surface 151 of the small-diameter portion 15 of the housing 10.

The dimples 911 and 921 which work to secure the lap of the open end portions 915 and 925 of the outer and inner cover walls 91 and 92 are formed on the bottoms 910 and 920 remotest from the open end portions 915 and 925. Therefore, if the distance between the open end portion 915 and the bottom 910 of the outer cover wall 91 or between the open end portion 925 and the bottom 920 of the inner cover wall 92 is changed from a set value due to some production errors, it will result in instability of the lap of the open end portions 915 and 925 and the side surface 151 of the housing 10. If the outer cover wall 91 is short of length, it may not be welded to the housing 10 firmly, which causes, in the worst case, the outer cover wall 91 to be separated from the housing 10 during use of the gas sensor 9.

SUMMARY OF THE INVENTION

It is therefore a principal object of the present invention to avoid the disadvantages of the prior art.

It is another object of the present invention to provide a simple structure of a gas sensor which provides for ease of installation of a protective cover on a cover mount, firm engagement of the protective cover with the cover mount, and/or ease of machining of the cover mount.

According to one aspect of the invention, there is provided a gas concentration sensor. The gas concentration sensor comprises: (a) a hollow cylindrical housing having an open end; (b) a sensor element disposed within the housing, the sensor element having a sensing portion projecting from the open end of the housing; and (c) a cover assembly made up of an outer cylindrical cover and an inner cylindrical cover each of which includes an open end portion and a body portion. The body portion of the inner cylindrical cover is disposed within the body portion of the outer cylindrical cover in a non-contact fashion. The open end portion of at least one of the outer and inner cylindrical covers has a shoulder which is placed in contact with the open end portion of the other cylindrical cover to establish a positional relation between the cover assembly and the housing which defines portions of the outer and inner cylindrical covers installed on an end side wall of the housing continuing from the open end thereof.

In the preferred mode of the invention, the open end portion of each of the outer and inner cylindrical covers has a side end wall greater in diameter than the body portion and a shoulder formed between the side end wall and the body portion. The shoulder of the inner cylindrical cover is placed in contact with the shoulder of the outer cylindrical cover to establish a positional relation between the open end portions of the outer and inner cylindrical covers which defines a given lap of the side end walls of the outer and inner cylindrical covers which is joined to the end side wall of the housing continuing from the open end thereof.

The housing has a large-diameter portion and a small-diameter portion on which the end side wall is defined and a step formed between the large-diameter portion and the small-diameter portion. The open end portion of the inner cylindrical cover may have a side end wall bent outward to define the shoulder. The shoulder is placed in contact with the step of the housing while the open end portion of the outer cylindrical cover is placed in contact with the shoulder of the inner cylindrical cover to defines a lap of the open end portions of the outer and inner cylindrical covers installed on the end side wall of the housing.

The open end portion of the outer cylindrical cover may have a side end wall and the shoulder formed between the side end wall and the body portion. The open end portion of the inner cylindrical cover may have an end wall bent outward to define a flange which is placed in contact with a surface of the open end of the housing and which engages at an end thereof with the shoulder of the outer cylindrical cover to secure a given lap of the open end portion of the outer cylindrical cover over the end side wall of the housing for installation of the cover assembly on the housing.

The open end portion of each of the outer and inner cylindrical covers may alternatively have a side end wall and a shoulder formed between the side end wall and the body portion. The side end wall of the inner cylindrical cover abuts at an end thereof on the open end of the housing. The shoulder of the inner cylindrical cover is placed in contact with the shoulder of the outer cylindrical cover to secure the lap of the side end wall of the outer cylindrical cover over the end side wall of the housing for installation of the cover assembly on the housing.

The shoulder of the open end portion of one of the inner and outer cylindrical covers may be placed in contact with the open end portion of the other cylindrical cover on a plane extending substantially perpendicular to a longitudinal center line of the cover assembly to secures areas of the outer and inner cylindrical covers installed on the end side wall of the housing.

The inner cylindrical cover is disposed within the outer cylindrical cover coaxially with each other. The shoulder of the open end portion of the one of the inner and outer cylindrical covers is placed in annular line contact with the open end portion of the other cylindrical cover.

According to another aspect of the invention, there is provided a gas sensor which comprises: (a) a hollow cylindrical housing having an open end in which a groove is formed; (b) a sensor element disposed within the housing, the sensor element having a sensing portion projecting from the open end of the housing; (c) a cover assembly made up of an outer cylindrical cover and an inner cylindrical cover each of which includes an open end portion and a body portion, the body portion of the inner cylindrical cover being disposed within the body portion of the outer cylindrical cover in a non-contact fashion, the open end portions of the outer and inner cylindrical covers having outwardly extending shoulders, respectively, which are placed in contact with each other and fitted within the groove of the housing; and (d) an extension formed around the groove of the housing. The extension is bent to urge the shoulders of the outer and inner cylindrical covers into engagement with each other to install the cover assembly on the housing.

In the preferred mode of the invention, the extension is welded to the shoulders of the inner and outer cylindrical covers so that a tip of the weld lies within a thickness of the shoulder of the inner cylindrical cover.

BRIEF DESCRIPTION OF THE DRAWINGS

The present invention will be understood more fully from the detailed description given hereinbelow and from the accompanying drawings of the preferred embodiments of the invention, which, however, should not be taken to limit the invention to the specific embodiments but are for the purpose of explanation and understanding only.

In the drawings.

DESCRIPTION OF THE PREFERRED EMBODIMENTS

Figure 1:
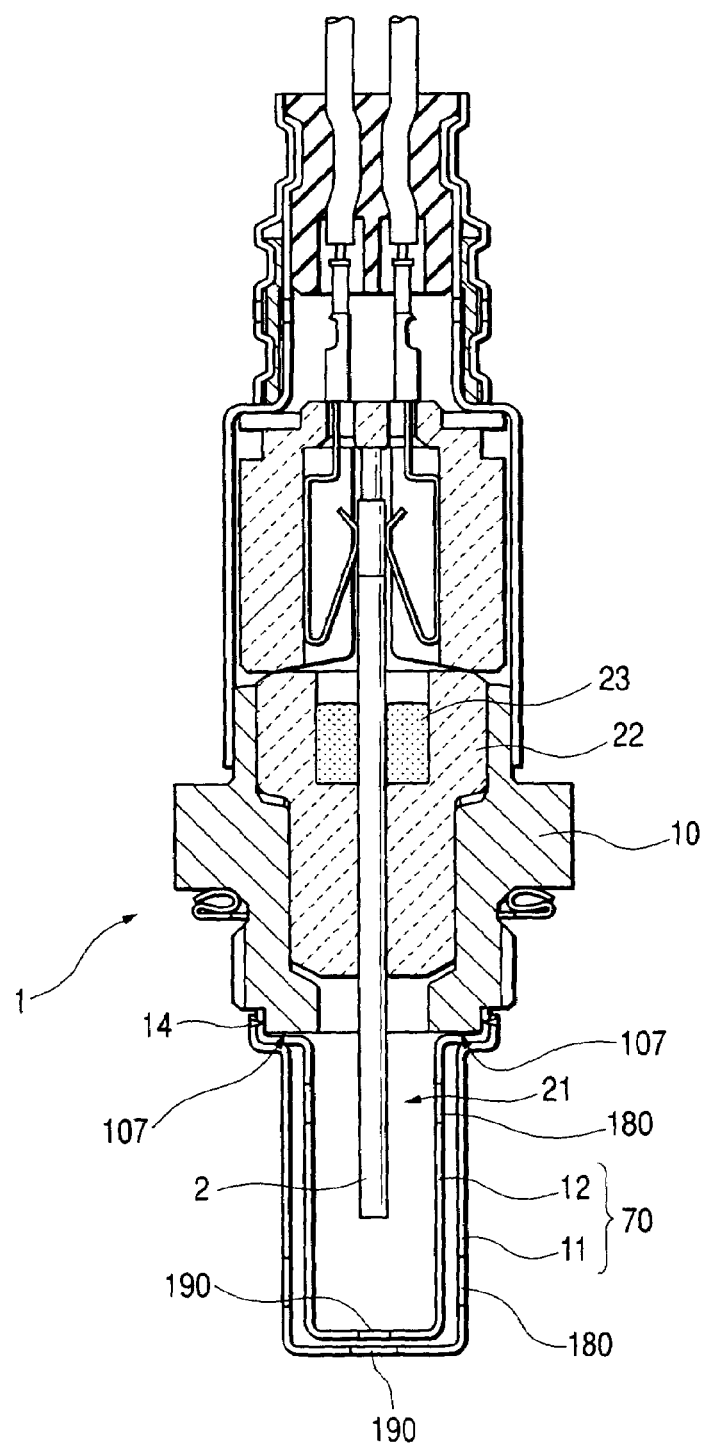
FIG. 1 is a longitudinal sectional view which shows a gas sensor according to the first embodiment of the invention.

Referring now to the drawings, wherein like numbers refer to like parts in several views, particularly to FIG. 1, there is shown a gas sensor 1 according to the first embodiment of the invention which may be employed in automotive air-fuel ratio control systems to measure $O_2$, HC, CO, or NOx contained in exhaust gasses of an internal combustion engine.

Figure 2:
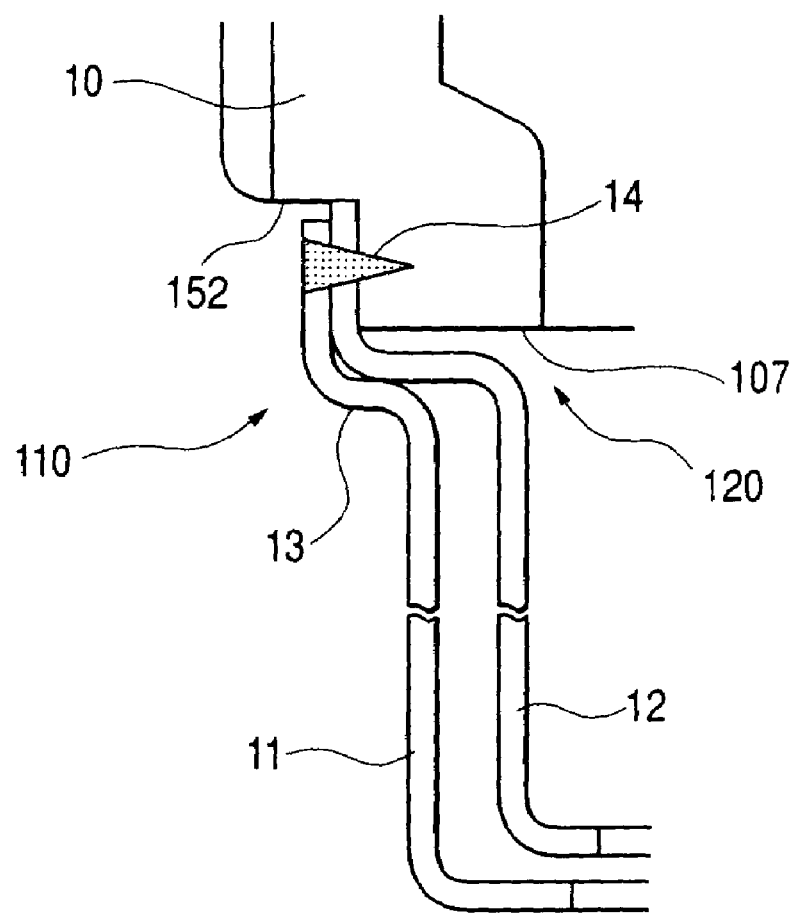
FIG. 2 is a partially sectional view which shows installation of a cover assembly to a housing in the first embodiment.
Figure 3A:
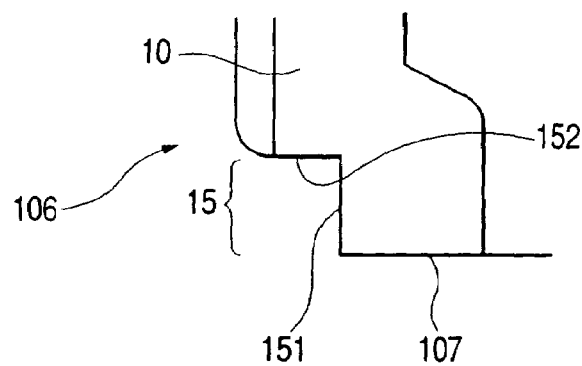
FIG. 3(a) is a partially sectional view which shows an end portion of a housing to which a cover assembly is installed.

The gas sensor 1 generally includes a hollow cylindrical housing 10, a sensing element 2, and a double walled protective cover assembly 70. The sensing element 2 is retained by an insulation porcelain 22 within the housing 10. The protective cover assembly 70 is installed on a side surface 106, as shown in FIG. 3(a), of an end portion of the housing 10 to cover a tip portion (i.e., a sensing portion) 21 of the sensing element 2 projecting outward from an end surface 107 of the housing 10. The protective cover assembly 70 is made up of an outer cylindrical cover 11 and an inner cylindrical cover 12 disposed within the outer cover coaxially with each other. The outer and inner covers 11 and 12, as clearly shown in FIGS. 2 and 3(b), have open end portions 115 and 125 each of which has an L-shape in cross section. The outer and inner covers 11 and 12 have body portions 118 and 128, respectively. The body portion 128 of the inner cover 12 is, as clearly shown in FIG. 1, disposed within the body portion 118 of the outer cover 11 in a non-contact form. The open end portions 115 and 125 expand outward to form annular shoulders 110 and 120. The shoulder 120 is so designed as to be fitted on the shoulder 110 in line engagement therewith to secure a given positional relation between the outer and inner covers 11 and 12 to define a lap of the open end portions 115 and 125 sufficient to be firmly attached to the periphery of a side surface 151, as shown in FIG. 3(a), of a small-diameter portion 15 of the housing 10.

The housing 10 is made of a metallic hollow cylindrical member. The sensing element 2 is made of a laminated plate such as one taught in U.S. Pat. No. 5,573,650, issued Nov. 12, 1996 to Fukaya et al., disclosure of which is incorporated herein by reference. A glass seal 23, as shown in FIG. 1, is fitted within the insulation porcelain 22 to establish an airtight seal between the sensor element 2 and an inner surface of the insulation porcelain 22.

Figure 4A:
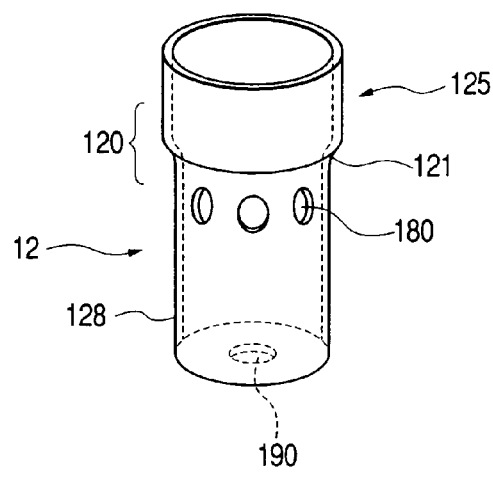
FIGS. 4(a) and 4(b) are perspective views which show an outer and an inner cover of a cover assembly.
Figure 4B:
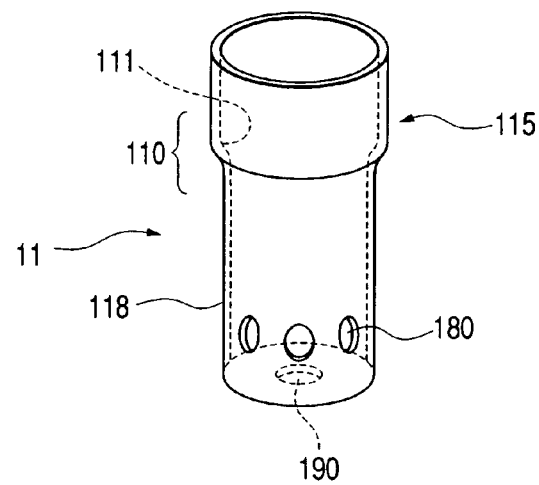

The outer and inner covers 11 and 12 have formed in the body portions 118 and 128 thereof, as respectively shown in FIGS. 4b and 4a, a plurality of gas holes 180 through which the gas to be measured flows into a gas chamber defined inside the inner cover 12. The outer and inner covers 11 and 12 also have formed in bottoms thereof holes 190 coinciding with each other.

The housing 10, as described above, has the small-diameter portion 15 formed on the tip portion thereof. The small-diameter portion 15, as clearly shown in FIG. 3(a), has the side surface 151 extending in parallel to a longitudinal center line of the housing 10 and leads to an annular horizontal surface 152 extending perpendicular to the longitudinal center line of the housing 10.

Figure 3B:
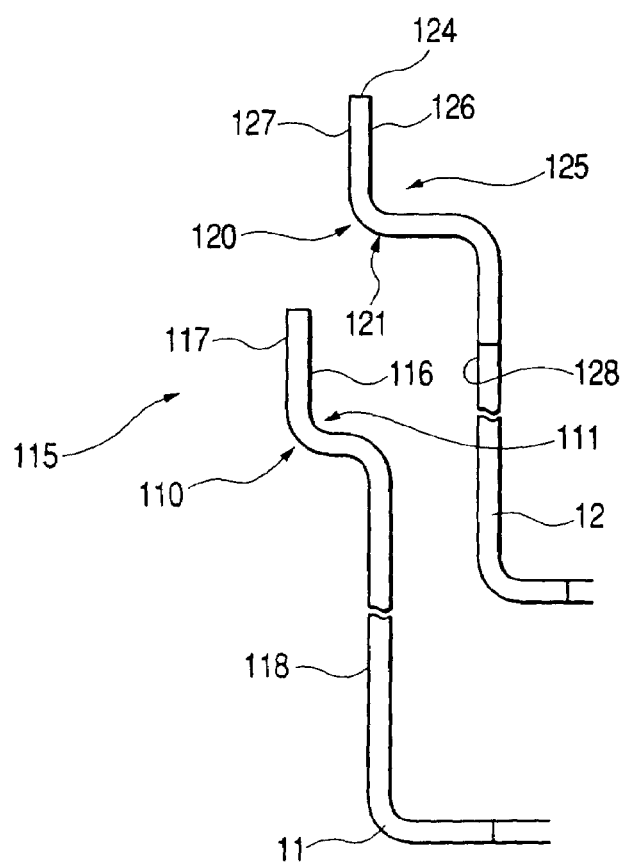
FIG. 3(b) is a partially sectional view which shows a cover assembly.

The open end portions 115 and 125 of the outer and inner covers 11 and 12, as described above in FIG. 3(b), expand outward to define the annular shoulders 110 and 120. The annular shoulders 110 and 120 have corners 111 and 121 which define an annular line contact 13, as shown in FIG. 2, on a horizontal plane extending perpendicular to a longitudinal center line of the cover assembly 70 when the outer cover: 11 is fitted on the inner cover 12. Instead of the annular line contact 13, the shoulder 120 may engage the shoulder 110 at a plurality of discrete point contacts. The open end portion 115 of the outer cover 11 also has, as shown in FIG. 3(b), an inner upright side surface 116 and an outer upright side surface 117. Similarly, the open end portion 125 of the inner cover 12 also has an inner upright side surface 126 and an outer upright side surface 127. The inner upright side surface 126 of the inner cover 12 is, as shown in FIG. 2, attached to the side surface 151 of the small-diameter portion 15 of the housing 10 in surface contact. The outer upright side surface 127 of the inner cover 12 establishes a surface contact with the inner upright side surface 116 of the outer cover 11 when the inner cover 12 is fitted within the outer cover 11. Further, the inner cover 12 has an end 124 which, as shown in FIG. 2, engages the horizontal surface 152 of the small-diameter portion 15 of the housing 10 directly.

The open end portions 115 and 125 of the outer and inner covers 11 and 12 are welded, as indicated at 14 in FIG. 2, to the side surface 151 of the small-diameter portion 15 of the housing 10 with the bottom of the inner cover 12 separate from that of the outer cover 11 through an air gap.

The installation of the protective cover assembly 70 on the housing 10 will be described below in detail.

First, the inner cover 12 is fitted on the small-diameter portion 15 of the housing 10 in direct contact of the inner upright side surface 126 with the side surface 151, and with the upper end 124 of the inner cover 12 forced into contact with the horizontal surface 152 of the housing 10.

Next, the outer cover 11 is put on the inner cover 12 in direct contact of the inner upright side surface 116 with the outer upright side surface 127 of the inner cover 12. The shoulder 110 of the outer cover 11 is fitted at the line contact 13 on the shoulder 120 of the inner cover 12, so that the open end portions 115 and 125 are lapped over each other around the periphery of the small-diameter portion 15 of the housing 10.

Finally, a lap of the open end portions 115 and 125 of the outer and inner covers 11 and 12 is welded, as indicated at 14 in FIG. 2, to the side surface 151 of the small-diameter portion 15 of the housing 10.

Specifically, the line contact of the shoulder 110 of the outer cover 11 with the shoulder 120 of the inner cover 12 secures a lap of areas of the open end portions 115 and 125 of the outer and inner covers 11 and 12 which is sufficient for providing the weld 14 to the small-diameter portion 15 of the housing 10, thereby enabling a firm joint of the protective cover assembly 70 to the housing 10 to be established regardless of dimensional errors of the inner and outer covers 11 and 12.

Figure 5:
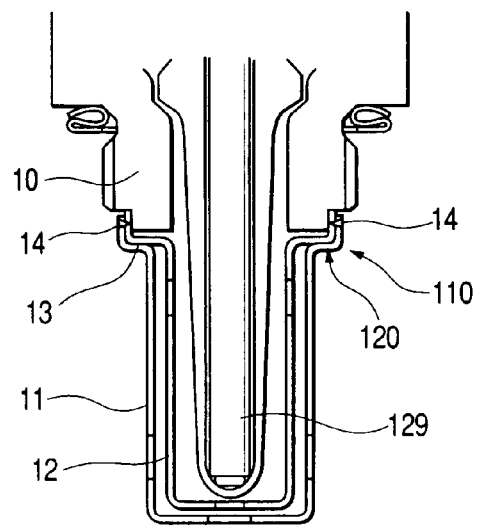
FIG. 5 is a partially sectional view which shows another type of sensor element which may be installed in the gas sensor of FIG. 1.

The sensing element 2 is, as described above, made of a laminated plate, but a cup-shaped sensing element 129, as shown in FIG. 5, on which a gas-measuring and a reference gas-measuring electrode layers are formed may alternatively be used.

Figure 6A:
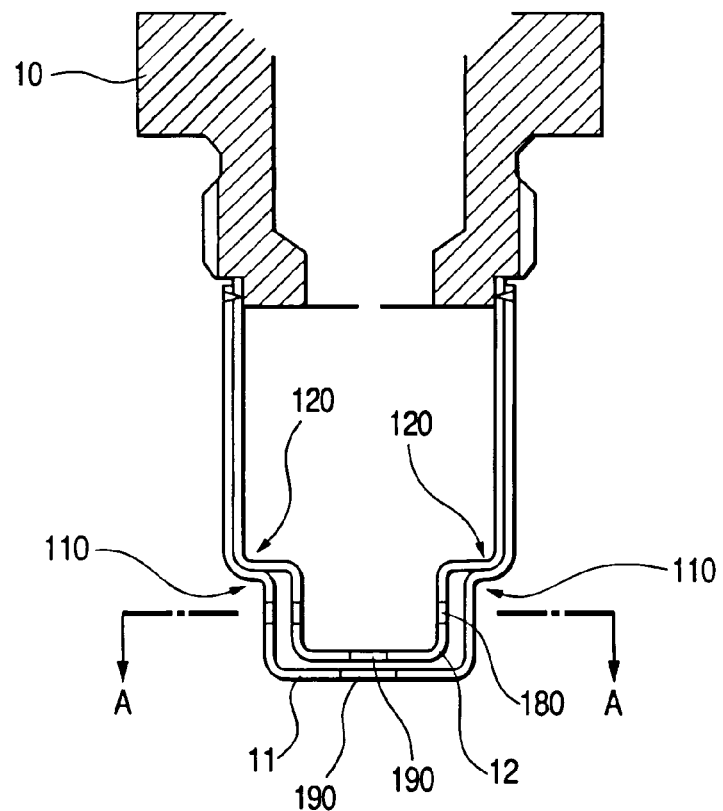
FIG. 6(a) is a sectional view which shows a modification of a cover assembly which may be installed on the gas sensor of FIG. 1.

The shoulders 110 and 120 of the outer and inner covers 11 and 12 may alternatively be, as shown in FIG. 6(a), formed closer to the bottoms of the inner and outer covers 11 and 12.

Figure 6B:
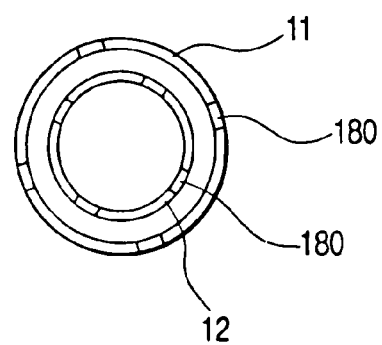
FIG. 6(b) is a lateral sectional view which shows the cover assembly of FIG. 6(a)

The gas holes 180 formed in the outer cover 12 are, as clearly shown in FIG. 6(b), shifted from those in the inner cover 11 in a circumferential direction.

Figure 7A:
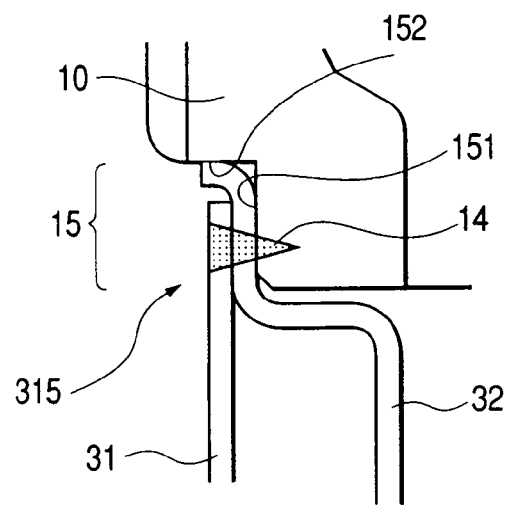
FIG. 7(a) is a partially sectional view which shows a cover assembly according to the second embodiment of the invention.
Figure 7B:
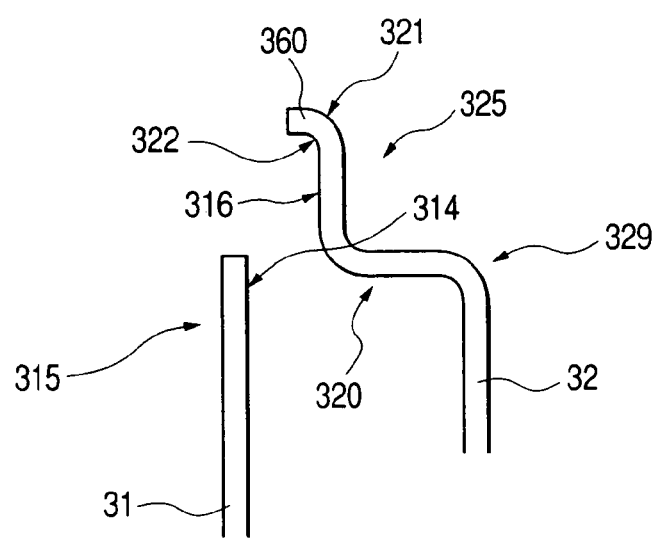
FIG. 7(b) is an exploded view which shows the cover assembly in FIG. 7(a)

FIGS. 7(a) and 7(b) show a gas sensor according to the second embodiment of the invention which is different from the first embodiment in that an inner cover 32 has a shoulder 320, while an outer cover 31 extends straight.

Specifically, the inner cover 32 has an open end portion 325 expanding outward, like the first embodiment, to form the shoulder 320 which has a laterally extending step 329. The open end 325 has a portion 321 curved outward to define a flange or second shoulder 360. The outer cover 31 has an open end 315 extending straight in parallel to the longitudinal center line of the housing 10.

The inner cover 32 is, as clearly shown in FIG. 7(a), fitted on the small-diameter portion 15 of the housing 10 in contact with the side surface 151. The curved portion 321 of the second flange 360 is placed in contact with the horizontal surface 152 of the housing 10. This secures a given positional relation between the inner cover 32 and the housing 10.

The outer cover 31 is put on the inner cover 32 with an inner wall 314 of the open end portion 315 lapped over an outer wall 316 of the open end portion 325 of the inner cover 32. The outer cover 31 abuts at an end thereof against an outer corner 322 of the second shoulder 360 of the inner cover 32. This establishes a given positional relation between the outer cover 31 and the inner cover 32. Specifically, the second shoulder 360 of the inner cover 32 works to position the end portion 315 of the outer cover 31 relative to the housing 10, thereby securing a lap of the open end portions 315 of the outer and inner covers 31 and 32 which is sufficient to be welded, as indicated at 14 in FIG. 7(a), around the periphery of the side surface 151 of the small-diameter portion 15 of the housing 10. Other arrangements are identical with those of the first embodiment, and explanation thereof in detail will be omitted here.

Figure 8:
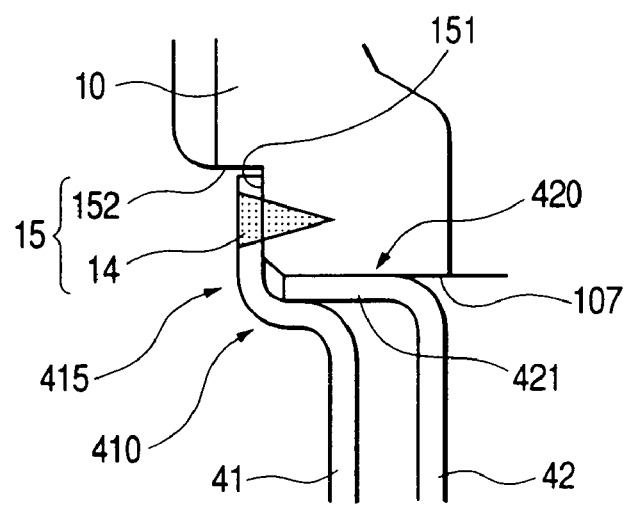
FIG. 8 is a partially sectional view which shows a cover assembly according to the third embodiment of the invention.

FIG. 8 shows a gas sensor according to the third embodiment of the invention.

The outer cover 41 has a shoulder 410, similar to the shoulder 110 in the first embodiment, formed on an open end portion 415 thereof. The inner cover 42 has an open end portion 420 bent outward at substantially right angles to define a flange or shoulder 421 which extends in parallel to the end surface 107 of the housing 10. The shoulder 421 is attached at an inner wall thereof to the end surface 107 of the housing 10, thereby securing the location of the inner cover 42 relative to the housing 10.

The outer cover 41 is put on the inner cover 42 with the shoulder 410 placed in an annular line contact with an end of the shoulder 421 of the inner cover 42, thereby retaining the inner cover 42 on the end surface 107 of the housing 10 and securing a lap of the open end portion 415 of the outer cover 41 over the side surface 151 of the housing 10 which is sufficient to be welded, as indicated at 14, around the periphery of the side surface 151 of the small-diameter portion 15 of the housing 10.

Other arrangements are identical with those in the first embodiment, and explanation thereof in detail will be omitted here.

Figure 9:
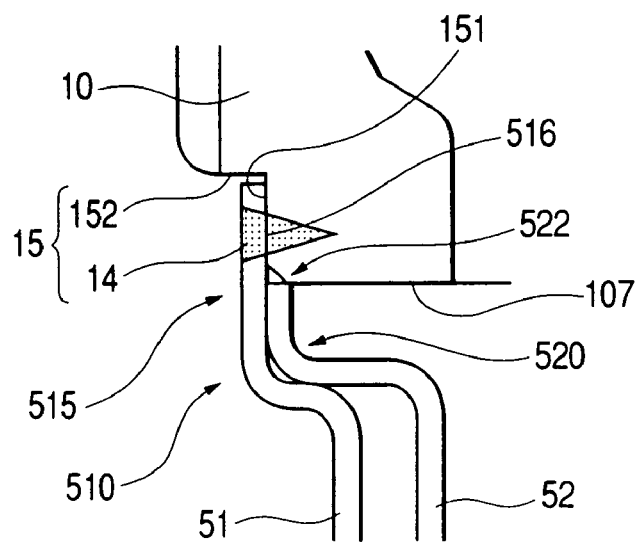
FIG. 9 is a partially sectional view which shows a cover assembly according to the fourth embodiment of the invention.

FIG. 9 shows a gas sensor according to the fourth embodiment of the invention.

The outer cover 51 and the inner cover 52, like the first embodiment, both have shoulders 510 and 520, but the shoulder 520 of the inner cover 52 abuts on the end surface 107 of the housing 10 without being welded to the side surface 151 of the housing 10.

Specifically, the outer cover 51 has a vertically extending open end portion 515 which has a length greater than that of the open end portion 115 in the first embodiment. The shoulder 520 of the inner cover 52 has an end 522 placed in contact with the end surface 107 of the housing 10. The outer cover 51 is fitted on the small-diameter portion 15 of the housing in contact of an inner upright side surface 516 thereof with the side surface 151 of the housing 10, thereby securing the location of the outer cover 51 relative to the housing 10. The outer cover 51 is welded as shown at 14, at the open end portion 515 thereof directly to the periphery of the small-diameter portion 15 of the housing 10 and holds the shoulder 520 of the inner cover 52 between the shoulder 510 thereof and the end surface 107 of the housing 10. The shoulder 520 of the inner cover 52 is, like the first embodiment, placed in line contact with the shoulder 510 of the outer cover 51, thereby securing a lap of the open end portions 515 of the outer cover 51 over the side surface 151 of the small-diameter portion 15 of the housing 10 which is sufficient for providing a firm joint of the protective cover assembly 70 to the housing 10.

The outer diameter of the shoulder 520 of the inner cover 52 may be slightly greater than the inner diameter of the open end portion 515 of the outer cover 51 for establishing a press fit of the shoulder 520 of the inner cover 52 within the shoulder 510 of the outer cover 51.

Figure 10A:
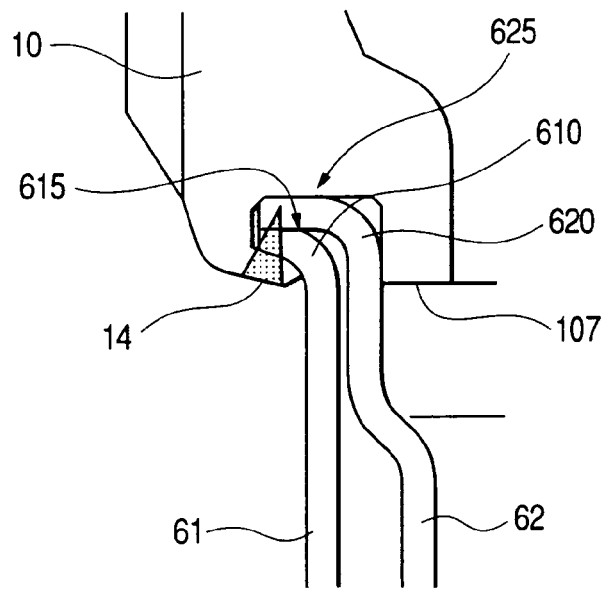
FIG. 10(a) is a partially sectional view which shows installation of a cover assembly in a housing according to the fifth embodiment of the invention.
Figure 10B:
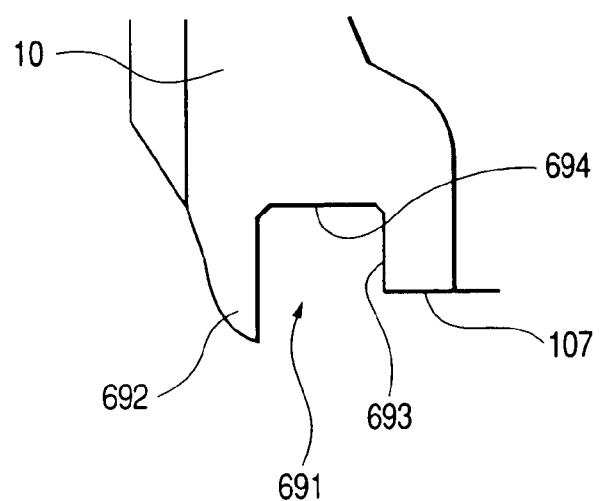
FIG. 10(b) is a partially sectional view which show an annular groove of a housing in which a cover assembly is installed.
Figure 11:
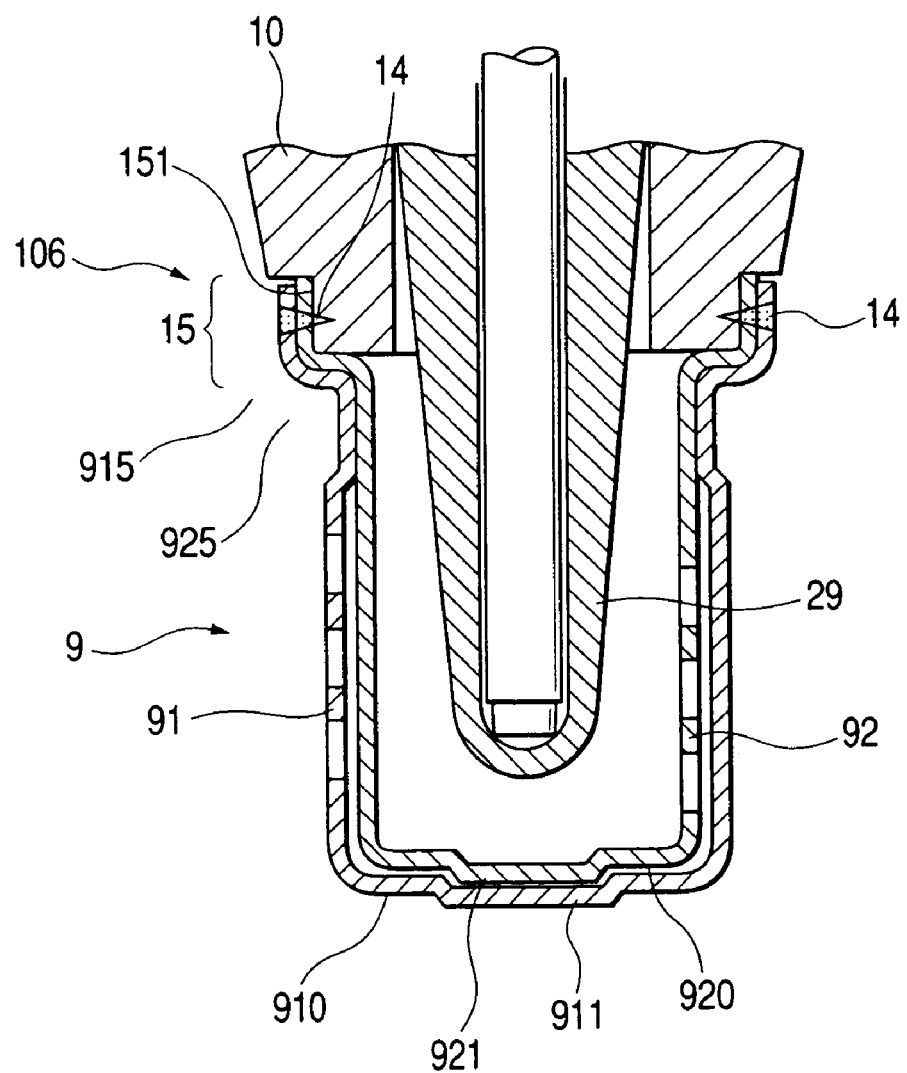
FIG. 11 is a longitudinal sectional view which shows a conventional gas sensor.

FIGS. 10(*a*) and 10(*b*) show a gas sensor according to the fifth embodiment of the invention.

The outer cover 61 has an open end portion 615 curved outward to form a shoulder 610. Similarly, the inner cover 62 has an open end portion 625 curved outward to form a shoulder 620. An upper portion of the inner cover 62, as viewed in FIG. 10(*a*), bulges slightly so as to lap over an upper portion of the outer cover 61. The housing 10 has, as clearly shown in FIG. 10(*b*), an annular groove 691 formed in the end surface 107 and an annular extension wall 692 formed around the periphery thereof.

The installation of the outer and inner covers 61 and 62 on the housing 10 is accomplished by fitting the open end portions 615 and 625 within the groove 691 of the housing 10 and bending the annular extension wall 692 inward to retain the shoulders 610 and 615 elastically within the groove 691 in contact with a side wall 693 and a bottom wall 694 of the groove 691, thereby establishing a firm fit within the groove 691. The annular extension wall 692 is welded, as indicated at 14 in FIG. 10(*a*), to the open ends 615 and 625 of the outer and inner covers 61 arid 62. The weld 14 extends inside of the open end portion 625 of the inner cover 62 without reaching the bottom wall 693 of the groove 691, thereby avoiding thermal damage to the housing 10.

While the present invention has been disclosed in terms of the preferred embodiments in order to facilitate better understanding thereof, it should be appreciated that the invention can be embodied in various ways without departing from the principle of the invention. Therefore, the invention should be understood to include all possible embodiments and modifications to the shown embodiments witch can be embodied without departing from the principle of the invention as set forth in the appended claims.

What is claimed is:

1. A gas sensor comprising:
    a hollow cylindrical housing having an open end in which a groove is formed;
    a sensor element disposed within said housing, said sensor element having a sensing portion projecting from the open end of said housing;
    a cover assembly made up of an outer cylindrical cover and an inner cylindrical cover each of which includes an open end portion and a body portion, the body portion of the inner cylindrical cover being disposed within the body portion of the outer cylindrical cover in a non-contact fashion, the open end portions of the outer and inner cylindrical covers having outwardly extending shoulders, respectively, which are placed in contact with each other and fitted within the groove of said housing; and
    an extension formed around the groove of said housing, said extension being bent to urge the shoulders of the outer and inner cylindrical covers into engagement with each other to install said cover assembly on said housing,
    wherein said extension is welded to the shoulders of the inner and outer cylindrical covers so that a tip of the weld lies within a thickness of the shoulder of the inner cylindrical cover.

2. A gas sensor comprising:
    a hollow cylindrical housing having an open end;
    a sensor element disposed within said housing, said sensor element having a sensing portion protecting from the open end of said housing; and
    a cover assembly made up of an outer cylindrical cover and an inner cylindrical cover each of which includes an open end portion and a body portion, the body portion of the inner cylindrical cover being disposed within the body portion of the outer cylindrical cover in a non-contact fashion, the open end portion of at least one of the outer and inner cylindrical covers having a shoulder which is placed in contact with the open end portion of the other cylindrical cover to establish a positional relation between said cover assembly and said housing which defines a portion of at least one of the outer and inner cylindrical covers fixed on an outer peripheral end side wall of said housing continuing from the open end thereof,
    the portion of the at least one of the outer and inner cylindrical covers being welded to said housing to install the outer and inner cylindrical covers on said housing.

3. A gas sensor comprising:
    a hollow cylindrical housing having an open end;
    a sensor element disposed within said housing, said sensor element having a sensing portion projecting from the open end of said housing; and
    a cover assembly made up of an outer cylindrical cover and an inner cylindrical cover each of which includes an open end portion and a body portion, the body portion of the inner cylindrical cover being disposed within the body portion of the outer cylindrical cover in a non-contact fashion, the open end portion of at least one of the outer and inner cylindrical covers having a shoulder which is placed in contact with the open end portion of the other cylindrical cover to establish a positional relation between said cover assembly and said housing which defines a portion of at least one of the outer and inner cylindrical covers fixed on an outer peripheral end side wall of said housing continuing from the open end thereof, wherein the open end portion of each of the outer and inner cylindrical covers has a side end wall greater in diameter than the body portion and a shoulder formed between the side end wall and the body portion, the shoulder of the inner cylindrical cover being placed in contact with the shoulder of the outer cylindrical cover to establish a positional relation between the open end portions of the outer and inner cylindrical covers which defines a given lap of the side end walls of the outer and inner cylindrical covers which is joined to the outer peripheral end side wall of said housing continuing from the open end thereof, the portion of the at least one of the outer and inner cylindrical covers being welded to said housing to install the outer and inner cylindrical covers on said housing.

4. A gas sensor comprising:

a hollow cylindrical housing having an open end;

a sensor element disposed within said housing, said sensor element having a sensing portion protecting from the open end of said housing; and a cover assembly made up of an outer cylindrical cover and an inner cylindrical cover each of which includes an open end portion and a body portion, the body portion of the inner cylindrical cover being disposed within the body portion of the outer cylindrical cover in a non-contact fashion, the open end portion of at least one of the outer and inner cylindrical covers having a shoulder which is placed in contact with the open end portion of the other cylindrical cover to establish a positional relation between said cover assembly and said housing which defines a portion of at least one of the outer and inner cylindrical covers fixed on an outer peripheral end side wall of said housing continuing from the open end thereof, wherein said housing has a large-diameter portion and a small-diameter portion on which the outer peripheral end side wall is defined and a step formed between the large-diameter portion and the small-diameter portion, and wherein the open end portion of the inner cylindrical cover has a side end wall bent outward to define the shoulder, the shoulder being placed in contact with the step of said housing while the open end portion of the outer cylindrical cover is placed in contact with the shoulder of the inner cylindrical cover to defines a lap of the open end portions of the outer and inner cylindrical covers installed on the outer peripheral end side wall of said housing, the portion of the at least one of the outer and inner cylindrical covers being welded to said housing to install the outer and inner cylindrical covers on said housing.

5. A gas sensor comprising:

a hollow cylindrical housing having an open end;

a sensor element disposed within said housing, said sensor element having a sensing portion protecting from the open end of said housing; and a cover assembly made up of an outer cylindrical cover and an inner cylindrical cover each of which includes an open end portion and a body portion, the body portion of the inner cylindrical cover being disposed within the body portion of the outer cylindrical cover in a non-contact fashion, the open end portion of at least one of the outer and inner cylindrical covers having a shoulder which is placed in contact with the open end portion of the other cylindrical cover to establish a positional relation between said cover assembly and said housing which defines a portion of at least one of the outer and inner cylindrical covers fixed on an outer peripheral end side wall of said housing continuing from the open end thereof, wherein the open end portion of the outer cylindrical cover has a side end wall and the shoulder formed between the side end wall and the body portion, the open end portion of the inner cylindrical cover having an end wall bent outward to define a flange which is placed in contact with a surface of the open end of said housing and which engages at an end thereof with the shoulder of the outer cylindrical cover to secure a given lap of the open end portion of the outer cylindrical cover over the outer peripheral end side wall of said housing for installation of said cover assembly on said housing, the portion of the at least one of the outer and inner cylindrical covers being welded to said housing to install the outer and inner cylindrical covers on said housing.

6. A gas sensor comprising:

a hollow cylindrical housing having an open end;

a sensor element disposed within said housing, said sensor element having a sensing portion protecting from the open end of said housing; and a cover assembly made up of an outer cylindrical cover and an inner cylindrical cover each of which includes an open end portion and a body portion, the body portion of the inner cylindrical cover being disposed within the body portion of the outer cylindrical cover in a non-contact fashion, the open end portion of at least one of the outer and inner cylindrical covers having a shoulder which is placed in contact with the open end portion of the other cylindrical cover to establish a positional relation between said cover assembly and said housing which defines a portion of at least one of the outer and inner cylindrical covers fixed on an outer peripheral end side wall of said housing continuing from the open end thereof, wherein the open end portion of each of the outer and inner cylindrical covers has a side end wall and a shoulder formed between the side end wall and the body portion, the side end wall of the inner cylindrical cover abutting at an end thereof on the open end of said housing, the shoulder of the inner cylindrical cover being placed in contact with the shoulder of the outer cylindrical cover to secure a given lap of the side end wall of the outer cylindrical cover over the outer peripheral end side wall of said housing for installation of said cover assembly on said housing, the portion of the at least one of the outer and inner cylindrical covers being welded to said housing to install the outer and inner cylindrical covers on said housing.

7. A gas sensor comprising:

a hollow cylindrical housing having an open end;

a sensor element disposed within said housing, said sensor element having a sensing portion protecting from the open end of said housing; and a cover assembly made up of an outer cylindrical cover and an inner cylindrical cover each of which includes an open end portion and a body portion, the body portion of the inner cylindrical cover being disposed within the body portion of the outer cylindrical cover in a non-contact fashion, the open end portion of at least one of the outer and inner cylindrical covers having a shoulder which is placed in contact with the open end portion of the other cylindrical cover to establish a positional relation between said cover assembly and said housing which defines a portion of at least one of the outer and inner cylindrical covers fixed on an outer peripheral end side wall of said housing continuing from the open end thereof, wherein the shoulder of the open end portion of the one of the inner and outer cylindrical covers is placed in contact with the open end portion of the other cylindrical cover on a plane extending substantially perpendicular to a longitudinal center line of said cover assembly to secures areas of the outer and inner cylindrical covers installed on the outer peripheral end side wall of said housing, the portion of the at least one of the outer and inner cylindrical covers being welded to said housing to install the outer and inner cylindrical covers on said housing.

8. A gas sensor comprising:

a hollow cylindrical housing having an open end;

a sensor element disposed within said housing, said sensor element having a sensing portion protecting from the open end of said housing; and a cover assembly made un of an outer cylindrical cover and an inner cylindrical cover each of which includes an open end portion and a body portion, the body portion of the inner cylindrical cover being disposed within the body portion of the outer cylindrical cover in a non-contact fashion, the open end portion of at least one of the outer and inner cylindrical covers having a shoulder which is placed in contact with the open end portion of the other cylindrical cover to establish a positional relation between said cover assembly and said housing which defines a portion of at least one of the outer and inner cylindrical covers fixed on an outer peripheral end side wall of said housing continuing from the open end thereof, wherein the inner cylindrical cover is disposed within the outer cylindrical cover coaxially with each other, the shoulder of the open end portion of the one of the inner and outer cylindrical covers is placed in annular line contact with the open end portion of the other cylindrical cover, the portion of the at least one of the outer and inner cylindrical covers being welded to said housing to install the outer and inner cylindrical covers on said housing.

* * * * *